United States Patent [19]

George

[11] Patent Number: 5,014,494
[45] Date of Patent: May 14, 1991

[54] METHOD OF STERILIZING MEDICAL ARTICLES

[75] Inventor: Robert D. George, St. Charles, Mo.

[73] Assignee: Sherwood Medical Company, St. Louis, Mo.

[21] Appl. No.: 249,979

[22] Filed: Sep. 27, 1988

[51] Int. Cl.⁵ .................. B65B 11/58; B65B 31/00; B65B 55/02
[52] U.S. Cl. .................. 53/425; 53/432; 53/434; 53/449
[58] Field of Search .......... 53/425, 432, 433, 434, 53/449; 422/22, 23, 24

[56] References Cited

U.S. PATENT DOCUMENTS

| | | | |
|---|---|---|---|
| 2,813,623 | 11/1957 | Colovos | 206/484 X |
| 2,904,392 | 9/1959 | Pomerantz | 422/23 |
| 3,315,802 | 4/1967 | Lonholdt et al. | 206/205 |
| 3,330,668 | 7/1967 | Hiscock | 53/449 X |
| 3,494,726 | 2/1970 | Barasch . | |
| 3,498,742 | 3/1970 | Long . | |
| 3,545,604 | 12/1970 | Gunther, Jr. | 53/425 X |
| 3,728,839 | 4/1973 | Glick | 53/425 |
| 3,754,700 | 8/1973 | Bonk . | |
| 3,926,309 | 12/1975 | Center . | |
| 4,150,744 | 4/1979 | Fennimore . | |
| 4,393,088 | 7/1983 | Matsusaka | 53/425 X |
| 4,433,244 | 2/1984 | Hogan . | |
| 4,436,700 | 3/1984 | Erickson . | |
| 4,467,065 | 8/1984 | Williams et al. . | |
| 4,660,721 | 4/1987 | Mykleby . | |
| 4,709,819 | 12/1987 | Lattuada et al. | 53/434 X |
| 4,714,595 | 12/1987 | Anthony et al. | 422/22 X |
| 4,744,199 | 5/1988 | Gannon | 53/434 |
| 4,779,398 | 10/1988 | Glandon et al. | 53/434 |
| 4,813,210 | 3/1989 | Masuda et al. | 53/425 |

Primary Examiner—Robert L. Spruill
Assistant Examiner—Linda B. Johnson
Attorney, Agent, or Firm—Andrew J. Beck; Montgomery W. Smith; Gene B. Kartchner

[57] ABSTRACT

In a method of radiation sterilization of medical articles, replacing the oxygen in the sterilization package with nitrogen prior to sterilizing prevents most of the brittleness and discoloration in the articles.

10 Claims, 1 Drawing Sheet

METHOD OF STERILIZING MEDICAL ARTICLES

TECHNICAL FIELD

The present invention relates to a method of sterilizing medical articles. In particular, the invention relates to a method of sterilizing plastic syringes so that the syringes will not be subject to yellowing and problems caused by micro-cracks.

BACKGROUND ART

Plastic syringes are commonly used for medical treatment, surgery and scientific research. Due to the invasive nature of these articles, which are most often used to pierce the skin of a patient, sterility and durability are of prime concern.

Radiation sterilization of syringes, often the preferred sterilization method, is known in the art. (See U.S. Pat. No. 3,315,802). Packaging for radiation sterilized syringes is generally light, pliable, and heat sealable. Both gas permeable and gas impermeable packaging may be used. Packaging materials commonly used include plastic films, paper adhesives and plastic/foil laminates. (See U.S. Pat. Nos. 3,315,802 and 2,813,623). Examples of suitable plastics are polyethylene and polyvinylchloride. Suitable foils include those produced from aluminum in combination with polymers.

Radiation sterilized syringes tend to become brittle, and lose durability with aging. Additionally, substantial yellow discoloring occurs. This discoloring is unpleasant to both patients and medical personnel since it lends a "used" appearance to the syringe that can result in a loss of patient confidence that syringes used on them are new and clean. Due to the possibility of contracting dangerous or even deadly disorders from re-used syringe needles, syringes that become noticeably yellow are sometimes unacceptable for their intended use. Also, because these articles increase in brittleness with age, the lengthy storage time which is common prior to use mandates a sterilization process which does not cause substantial brittleness, so that the articles will not crack or fall apart during use. The brittleness problem is compounded by the common practice of autoclaving prior to use to re-sterilize the outside of the container, to meet with hospital sterility requirements.

Thus, due to the requirement of sterile and durable medical articles which are not discolored, there exists a need for a radiation sterilization method that does not cause substantial yellowing or increased brittleness.

THE DRAWINGS

FIG. 1 is a flow diagram showing a preferred embodiment of the invention for use with gas impermeable packages; and FIG. 2 is a flow chart showing a second embodiment of the invention for use with gas permeable packages.

SUMMARY OF THE INVENTION

The present invention is directed to a method of radiation sterilization of medical articles such as plastic syringes which prevents most of the yellowing and increased brittleness inherent in present radiation methods. In the present method the articles are placed into either gas permeable or gas impermeable packaging, or other suitable material. Prior to radiation sterilization, the oxygen in the packages is replaced with a gas such as nitrogen or carbon dioxide which is non-reactive to the medical articles. Such replacement of oxygen by nitrogen prior to radiation prevents oxygen formation of free radicals on the surface of the articles which prevents much of the discoloration and loss of strength in the articles by preventing deterioration of their molecular integrity. Thus, the invention provides an economical method of sterilizing and preserving the new and sanitary appearance of plastic articles, especially disposable plastic syringes.

DESCRIPTION OF PREFERRED EMBODIMENTS

The present invention employs oxygen purging to prevent oxygen formation of free radicals on the surface of plastic articles prior to radiation sterilization. Although vacuum packaging alone accomplishes the oxygen purging purpose, it may cause shrinking of the container around the article. Therefore, although there is no oxygen present to form free radicals on the surface of the articles and thereby reduce their strength upon sterilization irradiation, the sterilized packages when simply vacuum packaged, will be of unequal size and formation.

Figure 1:
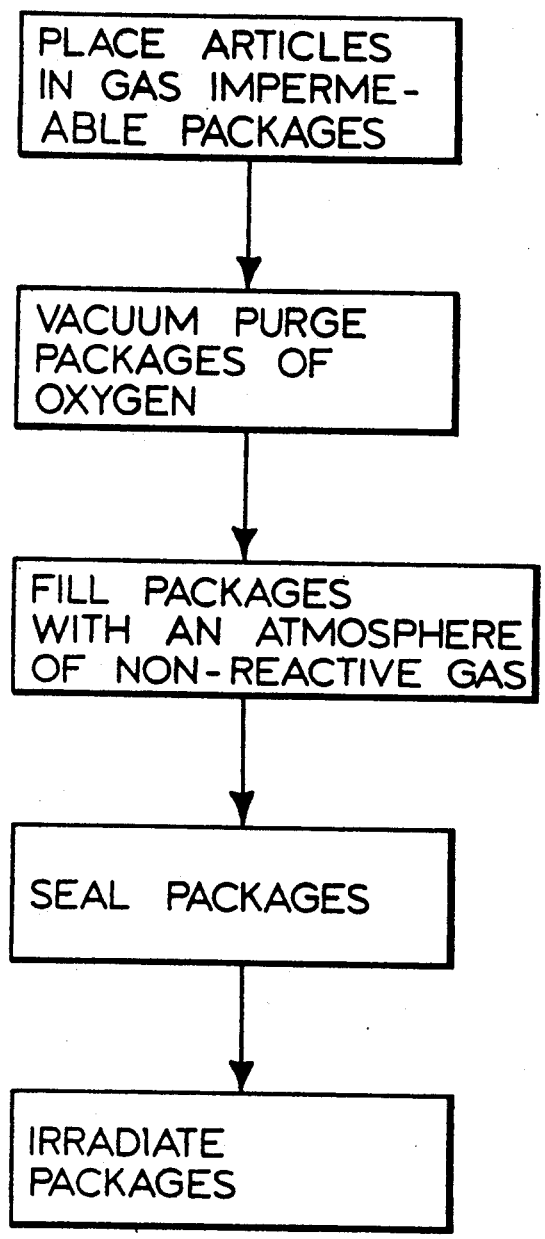

The invention may be used with gas impermeable packages or gas permeable packages. Referring first to FIG. 1 which shows in block diagram form a preferred embodiment of the invention using gas impermeable packages, the articles to be sterilized, e.g., polypropylene syringes, SILICONE CATHETERS, POLYVINYL CHLORIDE SUCTION INSTRUMENTS are first placed in ga impermeable packages such as conventional peel pouches. The packages may then be placed in a conventional container and vacuum purged of oxygen. In the next step, the packages are filled with an atmosphere of gas which is non-reactive to the syringes. Nitrogen maybe used for this purpose. The resultant packages are uniform in size, shape and general appearance.

After the nitrogen has been introduced, the packages are immediately sealed by a conventional device, for example, such as a needle probe sealer and in the final step the packages are irradiated. The step of irradiation must take place before oxygen is able to reenter the "impermeable" packaging. This reentry time varies according to the material of the packaging. Oxygen will re-enter paper the fastest, and plastics in an intermediate time. Foils keep oxygen out the longest and thereby provide the material suitable for longest storage prior to irradiation.

A radiation dosage of 3 Mrads of gamma radiation is the generally preferred dosage and wavelength type. However, depending on the density of the material used for the packaging, a range of 0.5 to 5 Mrads may typically be employed.

Figure 2:
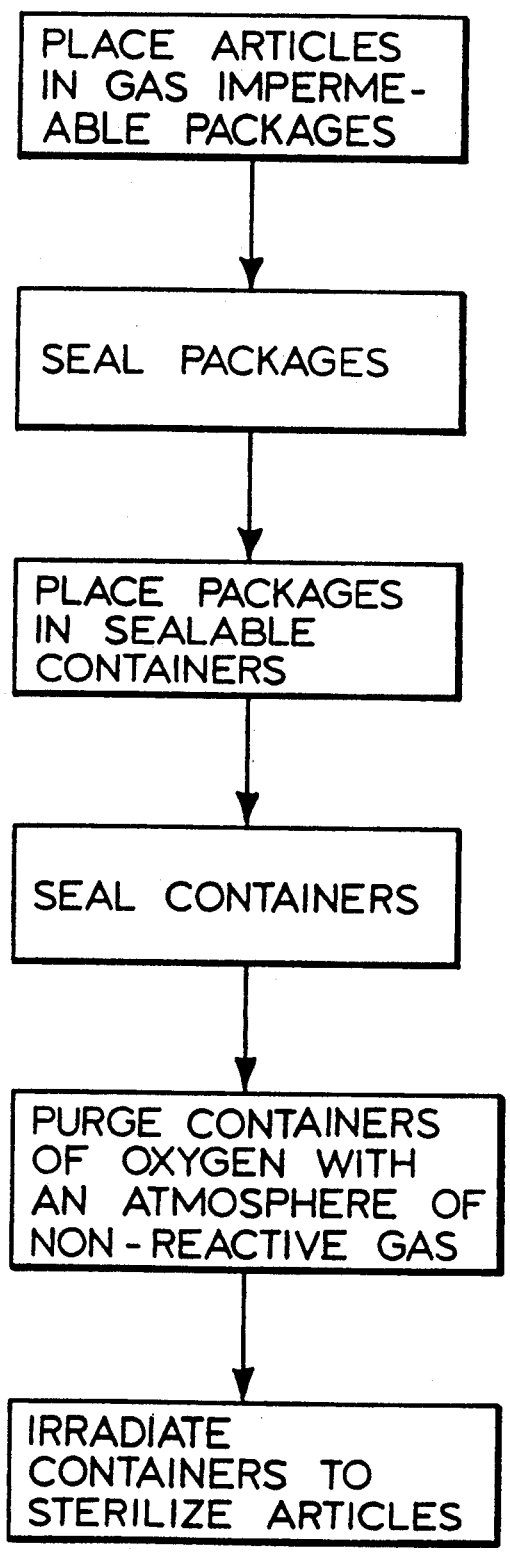

FIG. 2 shows how the invention may be used when it is desirable to package the articles to be sterilized in gas permeable packages. In this case, after the articles have been placed in the gas permeable packages, the packages are sealed and then placed in sealable containers such as tote pans into which a non-reactive gas such as nitrogen can be introduced. The tote pans are then sealed. Nitrogen is introduced into the sealed tote pan through an orifice, gradually replacing the oxygen in the packages containing the articles. This process, depending on the porosity of the packaging used can take from under a minute to several hours. Once the replacement of oxygen by nitrogen is complete, the tote pan containing the packaged articles is immediately radiation sterilized. Once sterilization has taken place, due to the gas permeable nature of the packages, oxygen will begin to replace nitrogen.

When packaging and sterilizing other articles, however, which may be susceptible to oxygen free-radical formation during storage, the type of packaging must be evaluated. A less expensive paper adhesive or plastic laminate may be unsuitable in these cases. More expensive foils generally preclude oxygen entry for an extensive period and should be employed where oxygen sensitivity in the storage process is a concern.

I claim:

1. A method of sterilizing medical articles which comprises:
   (a) placing the articles in gas permeable packages,
   (b) sealing the packages,
   (c) placing the packages in sealable containers,
   (d) sealing the containers,
   (e) pumping a non-reactive gas into the sealed containers,
   (f) permitting the packages to remain in the containers until the oxygen in the packages has been purged therefrom by the non-reactive gas, and
   (g) irradiating the packages and the articles to sterilize the latter while the packages are essentially purged of oxygen.

2. The method of claim 1 wherein the atmosphere of non-reactive gas is nitrogen.

3. The method of claim 1 wherein the articles are plastic syringes.

4. The method of claim 1 wherein the packages are irradiated in said containers.

5. The method of claim 1 wherein the packages are permitted to remain in said containers as described in step (f) for a period of time from under a minute to several hours to allow oxygen in the packages to be purged thereform.

6. A method of sterilizing a medical article which comprises:
   (a) placing at least one article in a gas permeable package,
   (b) sealing the package,
   (c) placing at least one package in a sealable container,
   (d) sealing the container,
   (e) pumping a non-reactive gas into the sealed container,
   (f) permitting the at least one package to remain in the container until the oxygen in the package has been purged therefrom by the non-reactive gas, and
   (g) irradiating the at least one package and the at least one article to sterilize the latter while said package is essentially purged of oxygen.

7. The method of claim 6 wherein the atmosphere of non-reactive gas is nitrogen.

8. The method of claim 6 wherein the at least one article is a plastic syringe.

9. The method of claim 6 wherein the at least one package is irradiated in the container.

10. The method of claim 6 wherein the package is permitted to remain in the container as described in step (f) for a period of time from under a minute to several hours to allow oxygen in the package to be purged therefrom.

* * * * *